United States Patent
Hughes et al.

(10) Patent No.: US 7,754,455 B2
(45) Date of Patent: Jul. 13, 2010

(54) BIOCATALYTIC MANUFACTURING OF (METH) ACRYLYLCHOLINE OR 2-(N, N-DIMETHYLAMINO) ETHYL (METH) ACRYLATE

(75) Inventors: Jonathan Hughes, Huddersfield (GB); Kenneth Charles Symes, Keighley (GB)

(73) Assignee: Ciba Specialty Chemicals Water Treatments Ltd., Bradford (GB)

( * ) Notice: Subject to any disclaimer, the term of this patent is extended or adjusted under 35 U.S.C. 154(b) by 728 days.

(21) Appl. No.: 10/591,775

(22) PCT Filed: Mar. 9, 2005

(86) PCT No.: PCT/EP2005/051046

§ 371 (c)(1),
(2), (4) Date: May 15, 2007

(87) PCT Pub. No.: WO2005/090586

PCT Pub. Date: Sep. 29, 2005

(65) Prior Publication Data

US 2007/0238156 A1    Oct. 11, 2007

(30) Foreign Application Priority Data

Mar. 19, 2004 (GB) ................... 0406217.0

(51) Int. Cl.
*C12P 7/62* (2006.01)
(52) U.S. Cl. ............ 435/135; 435/132; 435/183; 435/193
(58) Field of Classification Search ............ 435/135, 435/132, 193, 183
See application file for complete search history.

(56) References Cited

OTHER PUBLICATIONS

Masai Manabu et al., Journal of Pharmacological Sciences vol. 91. No. Supp. I, 2003, pp. 118P XP008049662.
Derwent Abst.No. 1992-137921 [71] of JP 4079889 Mar. 1992.
J. O'Sullivan et al., Biochimica et Biophysica Acta, vol. 450, No. 3, 1976, pp. 410-417.
Patel et al., Analytical Biochemistry, vol. 170, No. 2, 1988, pp. 355-360.

*Primary Examiner*—Irene Marx
*Assistant Examiner*—Susan Hanley
(74) *Attorney, Agent, or Firm*—Shiela A. Loggins

(57) ABSTRACT

A biocatalytic method for the synthesis of 2-(N,N-dimethyl amino)ethanol and/or choline esters of acrylic acid and/or methacrylic acid comprising reacting 2-(N,N-dimethylamino)ethanol and/or choline with acrylyl-CoA and/or methacrylyl-coA in the presence of a biocatalyst with choline acetyltransferase activity. The acrylyl-CoA and/or the methacrylyl CoA is formed by the reaction of acrylate and/or methacrylate with coenzyme A in the presence of ATP and a biocatalyst with S-acetyl coenzyme A synthetase activity.

6 Claims, No Drawings

BIOCATALYTIC MANUFACTURING OF (METH) ACRYLYLCHOLINE OR 2-(N, N-DIMETHYLAMINO) ETHYL (METH) ACRYLATE

This application is a national stage entry of PCT/EP05/51046 filed Mar. 9, 2005 which claims the benefit of priority to United Kingdom Application No. 040217.0, filed Mar. 19, 2005.

SUMMARY OF THE INVENTION

The invention relates to a biocatalytic method for the synthesis of choline and/or 2-(N,N-dimethylamino)ethanol (=DMAE) esters of acrylic acid and/or methacrylic acid, namely a method or process for the manufacture of acrylylcholine, methacrylylcholine, 2-(N,N-dimethylamino)ethyl acrylate (DMAEA hereinafter) and/or 2-(N,N-dimethylamino)ethyl methacrylate (DMAEMA hereinafter), comprising reacting choline and/or 2-(N,N-dimethylamino)-ethanol (DMAE hereinafter) with acrylyl-CoA and/or methacrylyl-CoA in the presence of a biocatalyst with choline acetyltransferase activity, where preferably the acrylyl-CoA and/or methacrylyl-CoA is formed by reaction of acrylate and/or methacrylate with coenzyme A in the presence of an energy providing substance and a biocatalyst with S-acetyl coenzyme A synthetase activity (acetyl CoA synthetase activity) or by reaction of acrylate or methacrylate that has been produced metabolically, for example from sugars e.g. via lactate by a microorganism; to (especially transformed, that is genetically modified) organisms having choline acetyltransferase activity and preferably in addition the acetyl CoA synthetase activity and their use in said process or method; the use of a biocatalyst with choline acetyltransferase activity to carry out the transfer of the (meth)acrylyl moiety from (meth) acrylyl CoA to choline and/or DMAE, in order to manufacture one or more of the choline or DMAE esters mentioned above; and to further uses, organisms, processes and methods as described below.

BACKGROUND OF THE INVENTION

The microbially or biocatalytically mediated conversion of biomass, e.g. cellulose or starch, to provide technically raw materials, is an important alternative to fossil fuels and is becoming of increasing importance in view of the future exhaustion of fossil fuels. Therefore it is important to have at hand as many biologically catalysed reactions as possible to allow for the use of biological or biocatalytical processes for their production.

Acrylylcholine, which is industrially more commonly referred to as qDMAEA, the quaternary salt of 2-(N,N-dimethylamino)ethyl acrylate, and methacrylylcholine, as well as DMAEA or DMAEMA, are (meth)acrylic monomers which find extensive use for the manufacture of polymers. Particularly water-soluble homopolymers or copolymers with other polymerisable monomers such as for instance (meth)acrylamide or n-vinylpyrrolidone or hydroxyethyl acrylate, and the like, are used in the manufacture of such polymers. These polymers find use in a number of applications, particularly for use as flocculating agents in the treatment of water; but also for other purposes, e.g. as thickeners, as retention aids in binders in the paper industry, as dispersants or as aids in the transfection of microorganisms with nucleic acids, such as DNA, and the like.

Choline (2-hydroxyethyltrimethylammonium) is a quaternary amino alcohol that occurs widely in living organisms as a constituent of certain types of phospholipids and in the neurotransmitter acetylcholine. It is also part of the daily diets as it is comprised in many foods.

DMAE [2-(N,N-dimethylamino)ethanol] also occurs widely in living organisms and is, for example, a precursor in the biosynthesis of phosphatidylethanolamine.

Acrylic acid and methacrylic acid are monomers used extensively to manufacture polymers, either as homopolymers usually of salts of the acid, such as sodium acrylate or ammonium acrylate, or a copolymers with other polymerisable monomers such as acrylamide and the like. These synthetic polymers are used for a variety of applications including flocculating agents for water treatment; coatings, finishes and binders for the paper, textile and leather industries; and use in the manufacture of paint, polishes and adhesives in the production of superabsorbents and dispersants and the like.

The metabolic synthesis of acrylic acid was described by Dalal et al (Biosources Digest vo. 2 p 89 to 97) in 1980. The authors reported that acrylyl CoA is hypothesised to be an intermediate in the anaerobic dehydration of lactate in *Megasphera elsdenii* and that it occurs following β-hydroxypropionyl CoA dehydration in *Clostridium propionicum*. They also suggested that using resting cells of *C. propionicum* acrylate accumulation was observed with propionate as the substrate. A metabolic scheme for the synthesis of acrylyl CoA is given in Scheme 1.

Scheme I: Metabolic pathways involving Acrylyl-AoA in Clostridium propionicum (see also Dalal et al., loc. cit.):

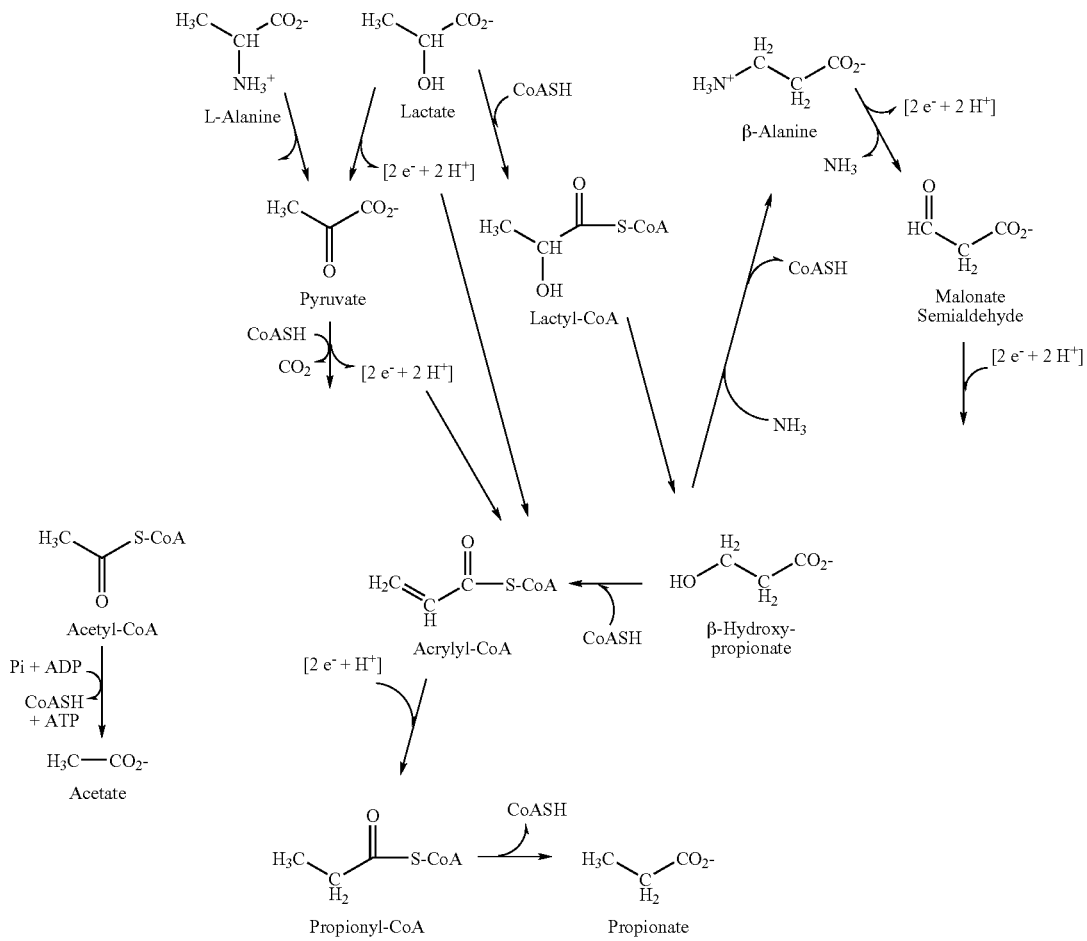

More recently, a few ways for the biosynthetic synthesis of acrylate and acrylate esters have been described, e.g. in WO 02/042418 A2 or WO 02/42471 A2, see also WO 00/71738 for the synthesis of acrylic acid.

Neither of these documents describes the possibility of manufacturing 2-(N,N-dimethylamino)ethyl acrylates or (methacrylates) or cholinylacrylates or -methacrylates(acrylylcholine or methacrylylcholine hereinbefore and hereinafter), and they usually require a combination of an acrylyl CoA-hydrolase and a lipase activity to first produce free acrylate from acrylyl CoA that is then converted into an ester of an aliphatic alcohol by means e.g. of a lipase.

On the other hand, EP 0 250 325 and WO 00/43348 describe chemical processes for the synthesis of acrylylcholine starting e.g. from 2-dimethylaminoethyl-acrylate and methyl chloride, while JP 9255640 and JP 6279371 describe methods for the chemical synthesis starting either from acrylonitrile reacted with sulphuric acid, via acrylamide sulphate as an intermediate and then with choline chloride, or for example reacting acrylic acid with choline chloride in the presence of an acid catalyst in toluene.

Instead of these chemical reactions, a biocatalytic reaction would, however, be highly desirable in order to provide the final step in an integrated biosynthetic approach that may also make use of renewable biomass.

Acrylic and methacrylic acid are known substrates of the enzyme S-acetyl CoA synthetase (S-acetyl coenzyme A synthetase, acetate thiokinase or acetate:CoA ligase) (EC 6.2.1.1), however, the products found did not in the main appear to correspond to the acyl CoA thioesters—instead binding of two equivalents of CoA took place via both Michael addition to the double bond and thioester formation via the carbonyl of the acid, and thus a bis-adduct was found to be formed (see e.g. Patel and Walt, Anal. Biochem. 170, 355-60 (1988)). The bis-adduct has the following formula:

5
6
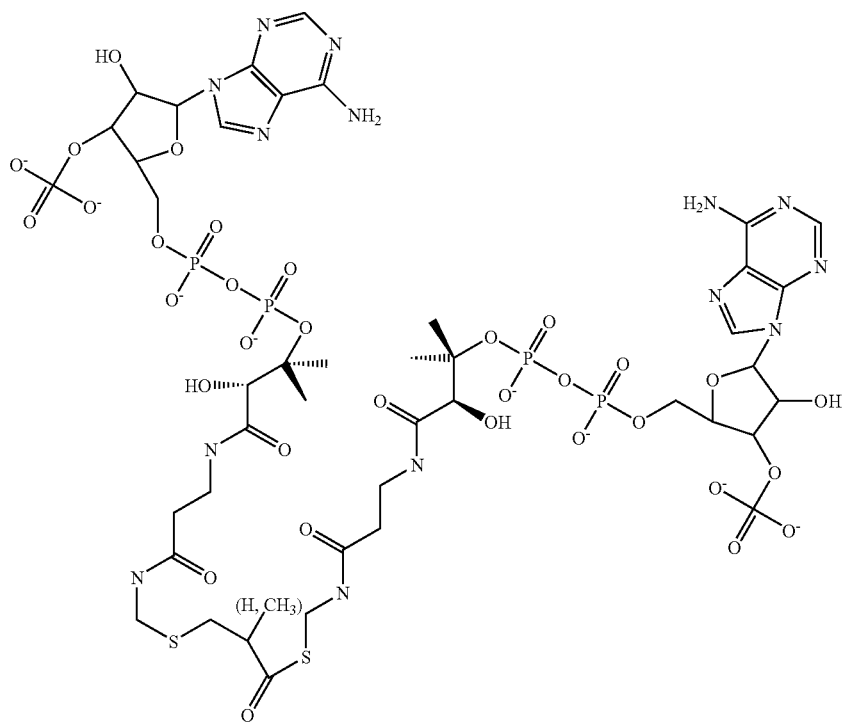

Against this background, it would be highly desirable to provide a biological process for the synthesis of (meth)acrylylcholine and/or DMAE(M)A that is simple and/or a real alternative to the present chemical methods and forms a basis also for the integration into a more general biotechnological process, e.g. finally making use of regenerative resources.

GENERAL DESCRIPTION OF THE INVENTION

Surprisingly it has now been found that it is possible to obtain (meth)acrylylcholine directly from S-(meth)acrylyl-Coenzyme A ((meth)acrylyl CoA) by reacting choline with acrylyl-CoA or methacrylyl CoA in the presence of a biocatalyst with choline acetyltransferase activity. In addition or alternatively, DMAEA and/or DMAEMA can be obtained using the same type of biocatalyst reacting DMAE with acrylyl-CoA and/or methacrylyl-CoA.

Even the synthesis of the precursor (meth)acrylyl CoA using methacrylic acid and/or acrylic acid and Coenzyme A with the help of a biocatalyst having acetyl CoA synthetase activity is possible because it can be shown that conditions are available where reaction of the carboxy group of the (meth) acrylic acid with the thiol group of Coenzyme A is favoured over addition to the double bond so that relatively more of the thioester than of the double bond adduct or bis-adduct can be formed, already in vitro using a biocatalyst that has acetyl CoA synthetase activity e.g. by optimising the concentration of reactants, especially relatively to each other. Especially preferred in this regard is a fed-batch process described in more detail below.

The surprising new insight that in vitro conditions allow for the synthesis of (meth)acrylyl Coenzyme A forms the basis of (meth)acrylylcholine and/or of DMAE(M)A synthesis also in vivo or by a combination of in vitro an in vivo steps.

This forms the basis for biosynthetic routes for the synthesis of (meth)acrylylcholine and/or DMAE(M)A that largely removes the dependency on petrochemical feedstocks, for example also by a combination of (meth)acrylyl-CoA synthesis in vivo or in vitro and (meth)acrylylcholine and/or DMAE(M)A synthesis in vitro or synthesis of (meth)acrylylcholine and/or DMAE(M)A with both steps in vivo.

DETAILED DESCRIPTION OF THE INVENTION

The invention, in a first aspect, relates to a process or method for the manufacture of acrylylcholine (very preferred), methacrylylcholine (preferred), 2-(N,N-dimethylamino)ethyl acrylate and/or 2-(N,N-dimethylamino)ethyl methacrylate, said process comprising reacting choline (preferred) and/or 2-(N,N-dimethylamino)ethanol with acrylyl-CoA and/or methacrylyl-CoA in the presence of a biocatalyst with choline acetyltransferase activity. Depending on the starting materials, the corresponding products are obtainable.

In a further aspect, the invention relates to a genetically modified organism (GMO) transformed with one or more (preferably recombinant) nucleic acids comprising one or more sections coding for and allowing the expression of a biocatalyst with choline acetyltransferase activity.

In another aspect, the invention relates to the use of a GMO as mentioned in the last paragraph for the manufacture of acrylylcholine (very preferred), methacrylylcholine (preferred), DMAEA and/or DMAEMA, comprising administering one or more appropriate starting materials derived from biomass and preferably also choline and/or DMAE to a culture of said microorganism and isolating the resulting product(s) acrylylcholine (very preferred), methacrylylcholine (preferred), DMAEA and/or DMAEMA.

The invention also relates to the (in vitro and/or in vivo) use of a biocatalyst with choline acetyltransferase activity to carry out the transfer of the (meth)acrylyl moiety from (meth)acrylyl CoA to choline (preferred) and/or DMAE to manufacture (meth)acrylylcholine (preferred) and/or DMAE(M)A.

The invention further also relates to the use of a biocatalyst with S-acetyl Coenzyme A synthetase activity for the manufacture of acrylyl CoA (especially with the corresponding reaction step taking place in vitro) with a low level of bis-adduct formation.

The reaction forming the basis of the present invention can be represented by the following reaction scheme:

SCHEME II:

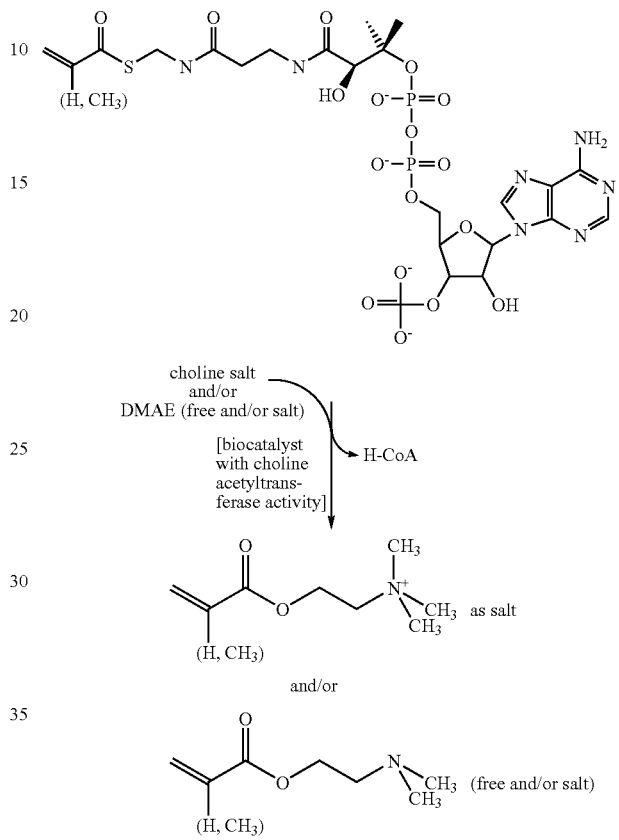

In Scheme II, the anion of the starting material choline (as salt) and/or the salt form of DMAE and the (meth)acrylylcholine and/or DMAE(M)A salt product may be any anion that can be tolerated in the respective reaction system, e.g. the anion of an organic acid, such as a sulphonate, e.g. methanesulphonate or toluenesulphonate, or a carboxylate, e.g. citrate or acetate, or especially an inorganic acid, such as sulphate, halogenide, e.g. chloride or bromide, nitrate, phosphate or the like.

Preferably, acrylyl- or methacrylyl-CoA is synthesized in vitro or in vivo from acrylic acid or methacrylic acid and/or salts thereof, commonly referred to as acrylate and/or methacrylate hereinafter, by means of a biocatalyst having S-acetyl CoA synthetase activity according to the following Scheme III:

Scheme III:

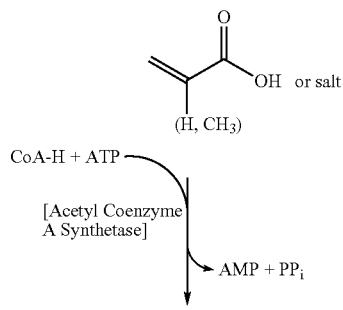

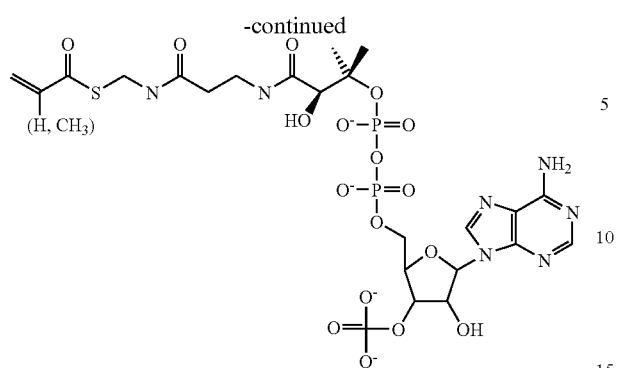
-continued

In contrast to the literature mentioned above, very surprisingly substantial amounts of (meth)acrylyl CoA can be obtained instead of the bis-adduct if the (in vitro) reaction conditions are modified appropriately.

Thus it has turned out that the reaction can result in more of the desired (meth)acrylyl CoA if the molar ratios of (meth)acrylate and CoA are such that the (meth)acrylate is used in a molar excess, e.g. a more than 2-fold molar excess, more preferably in a more than 4-fold molar excess, still more preferably in a more than 10-fold, e.g. an approximately 15-fold molar excess of (meth)acrylate over the CoA; for example, the concentration of (meth)acrylate may be in the range from 50 to 300, for example 120 to 280 mM and the CoA concentration a fraction thereof, preferably as derivable from the preferred molar excess ratios in favour of (meth)acrylate just mentioned.

Other components required are also present (e.g. a $Mg^{2+}$ salt, such as $MgCl_2$; ATP (preferably in hypostochiometric molar amounts in relation to the (e.g. alkaline metal, such as sodium) (meth)acrylate, e.g. in less than one $5^{th}$ of the molar amount of the (meth)acrylate, e.g. in 1/10 of this amount), and of course the biocatalyst, preferably the enzyme S-acetyl CoA synthetase, which is present in an appropriate activity, e.g. 0.5 to 15 units per ml in the presence of ATP, acetate and coenzyme A at 37° C. Preferably also buffer substances are present, for example Tris buffer (tris(hydroxymethyl)aminomethane or other buffer substances that allow for the establishment of an appropriate pH, e.g. in the range from 5 to 9, such as 6 to 8 (for example, about pH 6.4 to 7.3). These include any suitable biologically compatible buffers, such as phosphate buffers and the like.

The yield of the desired (meth)acrylyl CoA product over the bis-adduct is still improved if the coenzyme A is not added all at once but rather is added in smaller batches (the very preferred fed-batch approach) or continuously during the reaction, thus allowing for the thioester formation to take place before the addition of further Coenzyme A to the double bond of its product (meth)acrylyl CoA is possible. For example, the CoA may be added in amounts of 1/20 to 1/3 of the total final amount/concentration batchwise at intervals within a time period of, for example, up to 3 hours, e.g. 1/10 of the total CoA to be used at time 0, 5 min, 10, 15 and 20 min, respectively, then after 80, 95, 110, 120 min 145 and 155 min again 1/10 at these intervals. In addition, ATP may also be replenished where appropriate, e.g. to yield 5 mM concentration ATP is added at t=0, then again ATP is added to yield 5 mM concentration after 25 min and again to yield 5 mM ATP concentration after 150 min.

Where required, the enzyme may also be replenished after appropriate time periods.

Thus the hypostochiometric concentration of free CoA is kept preferably lower than a ratio of 1:100, e.g. 1:150 of the original (meth)acrylate concentration at each single time point, e.g. at 2 mM or lower, for example approximately 1 mM or lower, and more preferably the concentration of ATP is also kept below 1/20 of the initial concentration of (meth)acrylate at each time point, e.g. below 10 mM, for example at or below approximately 5 mM.

An interesting variant of the invention relates to the use of acrylic acid as only carbon source (e.g. assimilated into lactate and then pyruvate that can be used via the Krebs cycle) which in parallel is also fed into the reaction provided in Scheme III. This approach may provide especially good conditions for synthesis of acrylylcholine and/or DMAEA.

Instead of providing acrylate or methacrylate as precursors for the reaction with choline and/or DMAE in the presence of a biocatalyst with choline acetyltransferase activity, it is also possible to use appropriate starting materials derived from biomass. These precursors are the product of biological processes (including but not limited to waste biomass materials such as agricultural materials capable of being treated, for example hydrolysed, to release appropriate starting materials) and can first be converted via biochemical pathways into (meth)acrylyl CoA. Examples are sugars (e.g. from waste biomass materials, starch, cellulose or other polysaccharides), polyols (e.g. from fats), organic acids (e.g. from metabolism or from fatty acid ester hydrolysis), amino acids or the like. The (meth)acrylyl CoA can then be converted to (meth)acrylylcholine and/or DMAE(M)A as described herein. As biomass is renewable, this approach is basically very advantageous regarding sustainable development and environmental protection. In principle and advantageously it is also possible to derive the other starting materials, choline and/or dimethylaminoethanol, from biochemical pathways with biomass starting materials. For practical reasons, however, these starting materials may be added as such.

Some examples of possible metabolic reaction pathways and possible junction points as well as enzymatic activities where precursors can be fed in for the synthesis of acrylylcholine according to the invention are shown in Scheme I above as well as in Scheme IV presented below:

SCHEME IV:

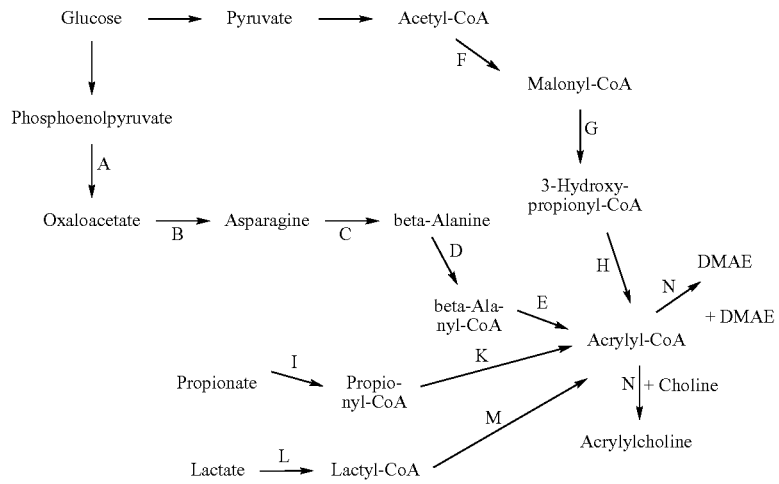

Here, the capital letters A to N preferably indicate the following enzyme activities:
A: phosphoenolpyruvate carboxykinase;
B: aspartate aminotransferase;
C: aspartate decarboxylase;
D: CoA transferase;
E: beta-alanyl CoA-ammonia lyase;
F: acetyl CoA-carboxylase;
G: malonyl CoA-reductase;
H: 3-hydroxypropionyl CoA-dehydratase (=acrylyl CoA-hydratase);
I: (acetyl) CoA-synthetase or (acetyl) CoA-transferase (which may be part of an enzyme complex such as OS17 in WO 02/042418);
K: propionyl CoA-reductase (which may be part of an enzyme complex such as OS17 in WO 02/042418);
L: CoA synthetase or CoA transferase;
M: lactyl CoA-dehydratase;
N: biocatalyst with choline acetyltransferase activity.

For the synthesis of methacrylylcholine, it is, for example, possible to use isobutyric acid or metabolic precursors thereof instead of propionic acid in Scheme IV as point of junction or as starting material.

Other educts are possible, e.g. using the route of oxidation of propylene which could be possible using *Mycobacterium convolutum* or genetic material for biocatalysts and biocatalysts obtainable therefrom to acrylate, the oxidation of allyl alcohol to acrylate (e.g. using *Pseudomonas fluorescens* or *Nocardia coralline* or genetic material for biocatalysts and biocatalysts obtainable therefrom) or acrylonitrile or methacrylonitrile using bacterial nitrilase or nitrile hydratase in combination with amidase activities, by for instance *Rhodococcus ruber* or *Rhodococcus rhodochrous*, respectively.

The corresponding pathways and enzymatic activities may be the result of gene expression (including transcription and translation and possible posttranslational modification) of nucleic acids that form part of the natural nucleic acid and genetic equipment of organisms, especially plants (or plant tissues) or more preferably microorganisms (especially unicellular organisms), most especially prokaryotes, e.g. bacteria, or (at least during a part of their life cycle) unicellular eukaryotes, for example fungi, such as yeasts, or they may be the result of the transformation of such cells (which are then becoming "host cells" for the introduced exogenous nucleic acids, that is genetically modified organisms (GMO)) comprising "exogenous" nucleic acids from other organisms (e.g. animals, such as rodents, or humans) or analogues thereof with the required sections coding for and capable of expressing the corresponding biocatalyst activities, preferably with recombinant nucleic acids, e.g. with vectors (e.g. plasmids, cosmids, viral or virus derived vectors or the like) that, in addition to one or more sections coding for the biocatalyst activities required for the synthesis of (meth)acrylylcholine and/or DMAE(M)A, or precursors thereof, may comprise one or more of repressor, activator, promoter and/or transporter sequences or other sequences required or useful for the integration, maintenance, transport within the cell or through cellular membranes, posttranslational modification and especially expression of the encoded polypeptides and their activities as well as optionally genetic markers allowing for selection (such as galactosidase or antibiotic resistance coding sequences) especially recombinant nucleic acid constructs carrying one or more of the genetic information constituents required for the biosynthesis of the corresponding enzymatic activities.

Examples of possible polypeptides and the underlying genetic information/nucleic acids that can be used to obtain enzyme activities directly useful in their parent organisms or useful in the transformation of different host cells are given in or can be deduced from WO 02/042418, and especially the corresponding nucleic acid and amino acid sequences as well as the methods therein for obtaining them or analogues thereof are incorporated by reference herewith. Methods useful in gene technology, especially for isolation, recombination, expression, transformation etc., are known to the person skilled in the art and can, for example, be based on or make use of the knowledge, methods and reagents disclosed in Sambrook et al., Molecular Cloning—A Laboratory Manual, 2nd edition, Cold Spring Harbor Press, 1989, or in Gassen et al., "Gentechnische Methoden—Eine Sammlung von Arbeitsanleitungen für das molekularbiologische Labor", Spektrum Akademischer Verlag, Heidelberg 1999, in F. M. Asubel (Hg.) "Short Protocols in Molecular Biology", 3rd ed., New York, Wiley 1997; or in Asubel et al., "Current Protocols in Molecular Biology", Vol. 1-3, Greene Publishing Associates and Wiley-Interscience, New York, 1987.

As an example, a hitherto unknown isolated enzyme with a biocatalytic activity useful in the present invention (e.g. choline acetyl transferase or S-acetyl CoA synthetase) may be partially sequenced, for example, using selective endoproteases for selective digestion, e.g. endo-protease Lys-C, endoprotease Glu-C, chymotrypsin, thermolysin or preferably trypsin (cleaving C-terminally from the basic amino acids arginine or lysine) and, after separation, e.g. electrophoretically on a gel or by chromatography (e.g. HPLC), determining the terminal sequences of the resulting peptides, e.g. by exopeptidases, e.g. carboxypeptidases, such as carboxypeptidase A, B or P). Preferred is tryptic digestion, then MS/MS analysis (TOF). The sequences thus obtained can then be used e.g. for finding corresponding coding nucleic acid (e.g. RNA or especially DNA) sequences or their non-coding counter strands, which may then be used to design primers to (e.g. by hybridization with genomic or partially (e.g. restriction endonuclease) digested DNA) find longer pieces of DNA coding for the corresponding enzyme (or the corresponding non-coding sequences from the partner strand in double-stranded DNA) which may then be pieced together (e.g. by gene walking) to a complete coding nucleic acid; or from cDNA libraries. By a combination of methods such as those depicted in the references mentioned in the last paragraph it is then possible to isolate the DNA coding for a polypeptide having one of the desired activities.

Alternatively, synthetic or isolated DNA (e.g. cDNA) of already published sequences coding for the corresponding biocatalytic activities, e.g. enzymes, for example choline acetyltransferase or S-acetyl CoA synthetase activity, or transporters, such as choline and/or DMAE transporters, may be used and integrated into vectors.

The term "nucleic acid" refers to polynucleotides, especially DNA. Where recombinant nucleic acids are mentioned, this is intended to mean specifically nucleic acids in the form of appropriate vectors, as well as the products resulting therefrom in the transformed host cells (e.g. due to integration into the genome including also plasmids or the like and concomitant changes, recombination or comparable events). Recombinant nucleic acids useful in the transformation of host organisms are, for example, vectors (e.g. plasmids, cosmids, viral or virus derived vectors or the like) comprising the coding sequences necessary for expression of the corresponding biocatalyst activities.

In general, "recombinant", wherever used in the context with a nucleic acid or especially DNA, is preferably having its customary meaning, for example including (1) a sequence that is not naturally occurring in the organism in which it is introduced or especially expressed or (2) a sequence made by an artificial combination of two otherwise separated shorter sequences (e.g. by insertion of a coding sequence into a plasmid or other vector). The artificial combination may be achieved by chemical synthesis and/or preferably by the artificial manipulation of isolated segments of nucleic acids, e.g. by genetic engineering techniques such as partial digestion, e.g. with endonucleases, ligation, splicing, or the like. "Recombinant" is also used to describe nucleic acid molecules that have been artificially manipulated but contain the same regulatory sequences and coding regions that are found in the organism from which the nucleic acid was isolated.

The invention relates also especially to a biosynthetic route to any one or more of acrylylcholine, methacrylylcholine, DMAEA and DMAEMA using a genetically modified organism (GMO) as well as the corresponding GMO, preferably a genetically modified (preferably (at least during parts of its life cycle) unicellular microorganism (especially a prokaryote, most preferably a bacterium, or a fungus, most preferably a yeast, but also insect cells may be employed, e.g. using baculovirus-expressed systems), which (either already in its natural form or after transformation with one or more appropriate nucleic acids) comprises a) a nucleic acid (especially a DNA) from a prokaryote, preferably a bacterium; or less preferably a eukaryote, such as yeast, other insect, fungal or plant cells, fungal or plant tissues or plants; each of which will enable the GMO to biocatalytically convert a biomass starting material (preferably as defined above, e.g. a polyol or a sugar such as glucose) preferably to lactate and further to (meth)acrylyl CoA;

b) in combination with one or more (preferably recombinant) nucleic acids (especially a DNA) from a higher organism (preferably an animal, more preferably an organism with choline acetyltransferase activity e.g. at the neuromuscular junction), such as an insect or especially a vertebrate, especially mammalian, tissue or cell which nucleic acid(s) code(s) for and express the required biocatalytic activities (especially enzymes) and enables the GMO to carry out the biocatalytic reaction between (meth)acrylyl CoA and a choline salt, such as choline chloride, and/or DMAE or a salt thereof. The choline salt or DMAE, or a salt thereof, can be supplied to the GMO in the growth medium. Alternatively, it can also be produced biosynthetically from appropriate starting materials derived from biomass.

Advantageously, the GMO, if not already displaying such activity, is also modified in addition to enable DMAE and/or choline to enter the cell and/or where required to allow the products DMAEA, DMAEMA, acrylylcholine and/or methacrylylcholine to leave the cell. The embodiments of this concept of combining the activities or recombinant genetic materials from microorganisms, especially prokaryotes or unicellular eukaryotes or plants with those of higher organisms, especially animals as described in the last paragraph, preferably mammalians, such as rodents or humans, e.g. taking genetic material coding for a choline acetyltransferase and preferably in addition a DMAE or for the preferred synthesis of the choline esters more preferably a choline transporter from the animal cells, such as the resulting GMO and their use in the manufacture of (meth)acrylylcholine and/or processes or methods using these GMO in the manufacture of (meth)acrylylcholine, are especially preferred variants of the invention, as especially the use of such GMO comprising recombinant nucleic acids coding for required activities in addition to the other required activities already present or also recombinantly integrated into said GMO in processes for the manufacture of DMAE(M)A and/or preferably (meth)acrylylcholine. The invention also relates to the manufacture of the respective GMO, especially unicellular organisms, especially prokaryotes, such as bacteria, e.g. *E. coli*, or fungi or single cell eukaryotes, e.g. yeasts, comprising combining one or more nucleic acids encoding the activities mentioned in this paragraph under a) and b). Preferred are a transformed prokaryote, especially a bacterium, or a transformed fungus, preferably a yeast, comprising one or more (natural or recombinant) nucleic acids coding for and especially allowing for the expression of choline S-acetyl transferase activity from prokaryotes or lower eukaryotes such as fungi, e.g. yeasts, and a (preferably recombinant) nucleic acid coding for and allowing for the expression of choline acetyltransferase activity of animals, especially rodents, such as rat, or humans (e.g. from human placenta).

The product DMAE(M)A and/or preferably (meth)acrylylcholine when produced in cells (e.g. GMO as mentioned in the last paragraphs) may be isolated from the supernatant directly (also in the case of permeabilized cells) or (if it is not readily leaving the cells) after permeabilization of the cells (which may also allow for the entry of starting materials, especially choline salts or DMAE in free and/or salt form), e.g. with appropriate surfactants or pore proteins (e.g. from the mammalian complement system) or after (e.g. chemical or mechanical) disruption of the cell membrane, e.g. using one or more methods employing a homogenizer, a blender, ultra sonic disruption or the like. In the case of disrupture remaining cells might be used for further production, e.g. if only parts of the culture are used for disruption, continuous reaction is possible but batch-wise production is preferred, while in the other cases the process may be led either in a continuous or a batch-wise way, the product being isolated from the supernatant.

Isolation of the product or products (DMAEA, DMAEMA, acrylylcholine and/or methacrylylcholine) in any case, also in the case of in vitro synthesis, may take place using standard methods, e.g. using chromatography (especially including a step of cation exchange chromatography), electrodialysis, solvent washing, extraction, partitioning or the like, or combinations of such methods. Alternatively, it may be possible to polymerise the DMAE(M)A and/or (meth)acrylylcholine in situ, either as a homopolymer or with the addition of other polymerisable monomers, for example acrylamide, styrene or the like, without need for prior purification.

It is also possible to reduce or (where the corresponding biocatalytic activities are not required for the survival of living cells where such are used) remove the activity of certain biocatalysts, e.g. by using one or more methods such as gene disruption, antisense nucleic acids, mutation, knock-out methods or administration of appropriate reversible or irreversible inhibitors, or the like in order to allow for the accumulation of desired products or intermediates, e.g. acrylyl CoA or methacrylyl CoA, by blocking metabolic pathways that lead away from these products other than the way used for their synthesis and preferably the further reaction to DMAE (M)A and/or especially (meth)acrylylcholine (e.g. one or more of the reactions catalyzed by or leading through the enzyme activities E, H, K or M shown in Scheme IV). This may be useful to achieve a higher availability (concentration) of precursors required for the synthesis of DMAE(M)A and/or (meth)acrylylcholine, e.g. (meth)acrylyl CoA.

While the borders for a distinction of in vitro and in vivo reactions may appear blurred in specific cases, these expressions are preferably defined as follows:

"in vitro", where used in this disclosure, preferably means that the corresponding process is carried out with cells or cell components (up to purified enzymes) that are no longer viable (that is, do no longer display all signs of life, that is motility, propagation, metabolism, heredity with or without mutability, and excitability) or with cell free systems, e.g. enzyme solutions.

"In vivo" means that a process takes place in the presence or preferably mainly inside of living substantially intact organisms or cells (which show the features of life as defined in the last paragraph). The term "substantially intact" is also intended to include organisms or cells with permeabilized membranes e.g. by means of surfactants or pore proteins or the like, as far as still the features of life defined in the last paragraph are still present.

Where (at least substantially) intact, such as (especially transformed, resulting in GMO) cells or organisms are to be used, it is especially useful if these have a DMAE or especially a choline transporter (especially one integrated into their respective cell membranes, e.g. as membrane protein) that allows for easy passage of DMAE or (in the preferred synthesis of the choline esters) choline through cellular membranes. Some examples for appropriate choline transporters in the form of choline transport proteins are: amino acid/ choline transporters, choline permeases, choline:sodium symporter activity, e.g. *P. aeruginosa* choline transporter BetT from *Pseudomonas aeruginosa* PAO1, or mammalian choline transporters, e.g. the Human protein Q9GZV3 High Affinity Choline Transporter, for gene structure see for example the sequence in the EMBL Genbank provided by Wieland et al. under http://harvester.embl.de/harvester/ Q9GZV3.htm or Apparsundaram et al., Biochem. Biophys. Res. Commun. 276, 862-7 (2000) or Okuda et al., FEBS Lett. 484, 92-7 (2000), or murine choline transporters, such as the murine hemicholinium-3-sensitive choline transporter cloned according to Apparsundaram et al., Biochem. Soc. Trans. 29, 711-6, 2001, or murine Slc5a7, rattus Cht1; insect choline transporters, e.g. *drosophila* CG7708; worms, such as *C. elegans* cho-1; or microbial choline transporters, e.g. a high affinity choline transport protein from *Escherichia coli, Haemophilus influenzae, Oceanobacillus iheyensis, Pseudomonas aeruginosa, Pseudomonas putida, Staphylococcus aureus, Staphylococcus epidermidis, Xanthomonas axonopodis, Yersinia pestis, Bordetella bronchiseptica* or *Bordetella pertussis*, from *Corynebacterium glutamicum* see for sequences http://66.93.129.133/transporter/wb/downloads/tree/faa/BCCT.faa, or from *Neisseria gonorrhoeae*, see http://www.stdgen.lanl.gov/cgi-bin/gene_id_search. cgi?dbname=ngon&gene_id=NG0529. In *Saccharomyces cerevisiae*, choline enters the cell via a single high-affinity transporter, Hnm1p. hnm1Δ cells lacking HNM1 gene are still viable (see e.g. Zufferey et al., Reexamining the Role of Transporter-Like (Ctlp) Proteins in Choline Transport, Neurochemical Research 29(2), 461-467 (2004)). A further description of choline transport in *Saccaromyces cerevisiae* is provided by Hosaka et al., J. Bacteriol. 143(1), 176-181 (1980). A description of the transporters for *Haemophilus influenzae* is given in Fan et al. in "Multiple Mechanisms for Choline Transport and Utilization in *Haemophilus influenzae*", Mol. Biol. 50(2), 537-548 (2003). The transport of choline into cells of *Halomonas elongate* to contribute to the osmoprotection of this organism is described by Canovas et al. in "Osmoprotectants in *Halomonas elongate*: High Affinity Betaine Transport System and Choline-Betaine Pathway", J. Bacteriol. 178(24), 7221-7226 (1996). Choline:H+ symporters in *Escherichia coli*, name BetK aka B0314, are known, and EP 1 236 739 describes choline transporters identified as 59914 and 59921 and their uses. These activities are, if not already present, preferably integrated by transformation of the respective microorganisms with appropriate nucleic acids that comprise one or more sections coding for and expressing the polypeptides and proteins responsible for said transporter activities.

Where required, also transporter molecules for the products (DMAEA, DMAEMA, acrylylcholine and/or methacrylylcholine) are present, either already as part of the natural equipment of the used organisms or as the result of genetic recombination and transformation.

Alternatively, cells may be used that have permeabilized cell membranes (e.g. by means of surfactants or pore proteins as already mentioned), or permeabilization and the presence of transporters may be combined.

If substantially intact organisms or cells are used as biocatalysts, e.g. in the process of a fermentation, a lower (usually meaning only minimal or no) addition of co-factors is required, so that this is a particularly preferred embodiment of the invention (while sometimes it may be necessary to contribute nutrients including precursors or vitamins useful in the biosynthesis of said co-factors). One of the reasons is that the cells are capable of recycling and sometimes even synthesizing the required co-factors (e.g. ATP, NAD(P)$^+$, NAD(P)H, FAD, FADH, Coenzyme A) by themselves.

However, the organisms/cells usually react very sensitively to high concentrations of organic substrates (substrate or product inhibition, solvent deactivation). Therefore, where specific solvents have to be used or where substrates or products might lead to a reduced reaction rate or yield, also the use of partially purified systems may be advantageous which forms a different embodiment of the invention. For partial purification, the cells are disrupted, and where desired the cell debris is removed and a cell-free extract is obtained.

The fermentation time is preferably so selected that an optimum with respect to the desired biocatalyst (e.g. choline acetyltransferase) activity is achieved. For example, when the cell density has reached an adequate value, the cultivation is discontinued. The culture broth is separated off in known manner, e.g. by centrifugation, and the sedimented cells are broken down in customary manner, e.g. by shaking with fine particular material such as glass beads, by ultrasound treatment, using a homogenizer, a blendor or a French press, or the like. Insoluble cell components and, if used, particular material such as glass beads or the like, are optionally removed, e.g., by centrifugation or filtration, and the particle and cell debris free residue is used as the biocatalyst activity source (crude extract). The residue, as a biocatalyst activity-comprising crude extract, can be used directly in the process according to the invention. Advantageously, however, in order to remove nucleic acids (viscous solutions) and other impurities or interfering components (e.g. inhibitors or disturbing enzyme activities or the like) the crude extract is subjected to further purification in order to obtain the biocatalytic activity or activities useful in the invention in more purified (more enriched) form. Preferably, the crude cell extract is subjected to one or more purification steps that, as such, are known in the art in order to remove interfering components from the extract.

The term "purified" means preferably "in at least partially purified form" (="in enriched form") or, more preferably, purified in the stricter sense, that is, in practically isolated form (e.g. in the case of isolated proteins, such as choline acetyltransferase or S-acetyl CoA synthetase) especially with more than 50, most especially more than 95% purity by weight compared to other oligo- or polypeptides present).

Further, the invention relates to the use of the mentioned organisms, which (here as in all other places where organisms are mentioned in the present disclosure) may preferably be GMO as mentioned above, such as (preferably transformed) plants or plant parts or plant tissues or insect cells or especially microorganisms, especially cells, more especially host cells for the respective recombinant genetic material (such as bacteria, e.g. *E. coli, K. lactis, Lactobacillus bulgaricus, Propionibacterium shermanii, Clostridium propionicum Zymomonas mobilis, Bacillus* spp. or *Bacillus coagulans*, for the case of extreme (e.g. temperature and/or pH) conditions archebacteriae, yeasts or other fungi, such as *Saccharomyces cerevisiae, Kluyveromyces* spp., *Pichia* spp., *Hansenulo* spp., *Candida* spp., *Trichosporon* spp. or *Yamadazyma* spp.) transformed with appropriate nucleic acids, in the production of one or more of the required biocatalysts, especially a biocatalyst with choline acetyl transferase or alternatively or in addition with S-acetyl coenzyme A synthetase activity, which may then be used in the manufacturing methods (in vitro, in vivo or combined) according to the invention for the synthesis of DMAEA, DMAEMA and/or especially acrylylcholine and/or methacrylylcholine.

Unless indicated otherwise already above or further below, further general terms, symbols and names used in the description of the present invention preferably have the following meanings (where more specific definitions, in each case separately, or in combination, may be used to replace more general terms in order to define more preferred embodiments of the invention, also as regards general terms, symbols and names and their explanations or preferred meanings already given above):

The term "biocatalyst", e.g. in "biocatalyst with (=having) choline acetyltransferase activity" or "biocatalyst with (=having) S-acetyl CoA synthetase activity", where used herein, relates to a biocatalyst having the respective (e.g. choline acetyltransferase or S-acetyl CoA synthetase) activity, especially an enzyme, most preferably a polypeptide, with said activity, such as most especially a choline acetyltransferase from rat, as described below, or S-acetyl coenzyme A synthetase (acetyl CoA synthetase) as described below. If not stated otherwise, all these terms include not only the naturally occurring, "authentic" sequence of a polypeptide of the invention, which are the preferred embodiments of the invention, but also all mutants, variants and fragments thereof which exhibit the respective (e.g. choline acetyl transferase) activity, preferably with at least 10% of the relative activity of the natural (parent) enzyme from which they are derived.

"A biocatalyst with choline acetyltransferase activity" especially means that the corresponding biocatalyst, preferably an enzyme, is active in standard assay systems used for determining the activity of choline acetyltransferase which catalyses the reaction of acetyl CoA with choline to acetylcholine and free coenzyme A. An appropriate test system is that used in Berry and Whittaker, Biochem. J. 73, 447-458 (1959). Biocatalysts useful in the invention here or in at least one of the subsequent assays advantageously show an activity of more than 0.01 nmoles/min per mg protein, more preferably of 0.1 nmoles/min per mg of protein, still more preferably of 0.4 nmoles/min per mg. or protein. Other methods for the determination of the activity of the enzyme (that are also applicable in the case of membrane bound or associated enzyme, e.g. measuring homogenates) are known, e.g. using $^{14}$C-labelled acetyl CoA, see for example Fonnum, F., Biochem. J. 115, 465-79 (1969) or Fonnum, F., J. Neurochem. 24, 407 (1975), or Rylett et al., J. Neurochem. 45, 611-20 (1993), for example determining the initial reaction velocities at 37° C. in a 40 µl reaction mixture containing 5-1200 µM [1-$^{14}$C] acetyl CoA (Amersham), 0.1-3.5 mM choline, 0.2-10 ng biocatalyst with choline acetyltransferase activity, 50 mM sodium phosphate (pH 7.4), 250 mM NaCl, 1 mM EDTA and 0.5 mg/ml BSA (see Ohno et al., Proc. Natl. Acad. Sci USA 98(4), 2017-22 (2001)). In one preferred exemplary method, in order to test the usefulness of a biocatalyst for synthetic purposes, for example first the choline acetyl transferase activity of the biocatalyst to be tested is determined using its natural substrate acetate. Then a solution of 7 mM choline chloride is prepared in pH 7.46 buffer (1.1 mM Na$_2$HPO$_4$/0.7 mM NaH$_2$PO$_4$). The choline solution (3 ml) is incubated at 37° C. for 15 min. Acetyl CoA (2 mg, 2.5 µmoles) and 0.1 ml of pH 7.4 choline acetyltransferase or the biocatalyst to be examined (for example with an activity of e.g. approximately 5.5 to 20 nmoles/min regarding acetate) is added and the absorbance measured with time. On completion of the reaction, the reaction mixture is stored frozen until analysed by ion chromatography (IC). IC analysis is carried out on a Dionex DX-300 instrument with an IonPac CS12A column, a mobile phase of 90% 20 mM methanesulphonic acid/10% of a 90% (v/v) solution of acetonitrile in water and conductivity detection (CSRS autosuppression external water mode cation regeneration system). After 435 min, 0.10 mM acetylcholine can be found with the enzyme having a presumed initial activity of 20 nmoles/min. A biocatalyst having sufficient activity should, in this test system, advantageously provide more than 0.02 mM acetylcholine under these conditions. More preferably, the activity with methacrylyl-CoA or preferably acrylyl-CoA should be more than 10%, still more preferably more than 50% in any used test system of the activity with acetyl-CoA for a biocatalyst with choline acetyltransferase activity that is particularly useful in a process or method of the present invention. Examples for enzymes with choline acetyltransferase activity are those from homo sapiens, or other vertebrates, such as mice or especially rat, or more generally from other metazoa. Also recombinant Choline acetyl transferases are included here, such as advantageously recombinant rat choline acetyl transferase AG220 from Chemicon International Inc., Temecula, Calif., or analogues thereof.

"A biocatalyst with acetyl CoA synthetase activity" especially means that the corresponding biocatalyst, preferably an enzyme, is active in standard assay systems used for determining the activity of acetyl CoA synthetase. For example, the following coupled enzyme test monitoring the formation of AMP may be used to determine acetyl CoA synthetase activity: The assay consists of ATP (2.5 mg, $5 \times 10^{-3}$ mmol), CoA (0.46 mg, $6 \times 10^{-4}$ mmol), $MgCl_2$ (4 mg, $2 \times 10^{-2}$ mmol), phosphoenolpyruvate (0.19 mg, $9.4 \times 10^{-4}$ mmol), KCl ($1.2 \times 10^{-4}$ mmol), NADP (0.25 mg, $3.6 \times 10^{-4}$ mmol), acetic acid ($10^{-1}$ to $10^{-4}$ mmol), acetyl coenzyme A synthetase or the biocatalyst to be tested (preferably in an activity of approximately 0.5 units), pyruvate kinase/lactate dehydrogenase (1 unit), myokinase (1 unit) and made up to a total volume of 1 ml with Tris buffer (0.25 M, pH 7.2). The reaction is monitored by observing the decrease in absorbance at 340 nm due to the oxidation of NADH to NAD+. The $V_{max}$ and binding constants are calculated by Lineweaver-Burk and Eadie-Hofstee plots. Other determination methods are possible, e.g. using acetyl-CoA formation coupled to reduction of NAD+ via malate dehydrogenase and citrate synthetase, e.g. as described by Cai et al., J. Bacteriol. 182, 2113-8 (2000) or Charles et al., Genetics 146, 9877-82 (1997). Particularly preferred is the method employed by Sigma for the testing of choline acetyl transferase activity which is a modification of the method described by Berg, P., J. Biol. Chem. 222, 991-1013 (1956): Here, acetyl CoA formed is converted with hydroxylamine into acetyl-NHOH, The latter is then mixed with a $FeCl_3$ solution to give a brown-colored product the absorbency of which is then measured at 546 nm, 1 cm light path. In brief, the final assay concentrations of the reaction mix (1.10 ml per vial) are: 136 mM potassium phosphate, 4 mM magnesium chloride, 9.1 mM ATP, 45 mM potassium fluoride, 9.1 mM potassium acetate, 9.1 mM reduced glutathione, 0.35 mM coenzyme A, 182 mM hydroxylamine and 0.02-0.04 units S-acetyl coenzyme A synthetase, the latter added in a volume of 0.1 ml after equilibration of the remaining solution at 37° C. The pH is 7.5. After addition of the enzyme, the mixture is immediately mixed and incubated for 20 min. After that, 2 ml of a 370 mM $FeCl_3$/3.3% trichloroacetic acid solution is added, followed by mixing with conversion and transfer to the measuring cuvettes. In the blank sample, acetyl CoA is missing. Preferably, a biocatalyst with S-acetyl CoA synthetase activity useful in the present invention in the preceding assay systems has an activity that is in the area of more than 0.0005 units per mg protein, more preferably in the area from 0.001 to, for example, 15 units per mg. protein, a unit being defined as the amount of biocatalyst forming 1.0 µmole of S-acetyl Coenzyme A from acetate, ATP and coenzyme A per min at 37° C. and pH 7.5. In order to test the CoA synthetase activity on a preparative scale, a reaction (e.g. at a 7 ml scale) can be started and conducted in 10.8 mM sodium phosphate/1.4 mM sodium hydroxide buffer as follows: A solution of 7.4 mM sodium acetate and 0.75 mM CoA is prepared and incubated at 37° C. for 15 min. S-acetyl-coenzyme A synthetase, either from Sigma, catalogue No. A 1765 from Bakers yeast, or the biocatalyst to be tested (e.g. 0.2 mg) and 28.4 mg ATP is added. The mixture (pH about 7.36) is then incubated at 37° C. in quartz cuvettes and the absorbance of the mixture at 232 nm is measured with time. For example, an initial activity of approximately 1 to 600 nmoles formation of acetyl CoA per minute or more is found in this assay. The preferred activity of this type for the preparation of (meth)acrylyl CoA (effect as (meth)acrylyl CoA synthetase activity) can advantageously be shown as described in the Examples. Preferably, the S-acetyl CoA synthetase activity for formation of methacrylyl-CoA or preferably acrylyl-CoA in the presence of acrylate or methacrylate should be more than 10%, still more preferably more than 50% in at least one test system for the determination of the activity for formation of acetyl-CoA for an biocatalyst with acetyl CoA syntetase activity that is particularly useful for a process or method according to the present invention. Examples for enzymes with acetyl CoA synthetase activity are acetyl CoA synthetase from yeast, e.g. baker's yeast (obtainable e.g. from Sigma or Roche), from bacteria, e.g. *Salmonella enterica, Sinorhizobium meliloti, Rhodospirillum rubrum*, from higher animals, e.g. beef heart or pigeon liver, or plants.

Where acids are mentioned, this is intended to encompass both the free acids as well as salts thereof, or mixtures thereof, e.g. metal- or ammonium salts or the like. Usually within the present disclosure acids are referred to in the form of the corresponding anions, e.g. as acrylate or acetate.

"(Meth)acrylyl" means acrylyl and/or methacrylyl. The invention preferably refers to the manufacture of methacrylylcholine or especially acrylylcholine (the latter may also be referred to as the N-methylated quaternary salt of 2-(N,N-dimethylamino)ethylacrylate) and the corresponding precursors, e.g. methacrylyl-CoA or especially acrylyl-CoA.

DMAE(M)A means 2-(N,N-dimethylamino)ethyl acrylate and/or 2-(N,N-dimethylamino)ethyl methacrylate).

Where choline, acrylylcholine or methacrylylcholine are mentioned in the present disclosure, this is intended to include the free "onium" ions (with a positively charged nitrogen) or the complete salt form with a counter ion, or both as appropriate.

DMAE as well as DMAE(M)A can be present in the free form and/or the (acid addition) salt form, any one of these or both forms being included where DMAE, 2-(N,N-dimethylamino)ethanol, DMAE(M)A or 2-(N,N-dimethylamino)ethyl acrylate or 2-(N,N-dimethylamino)ethyl methacrylate are mentioned.

Salts can, for example, be the salts with anions mentioned under Scheme II, acid additions salts those of the corresponding acids.

Further Preferred Embodiments of the Invention

In a further preferred embodiment of the invention, the invention relates to a process or method for the manufacture of DMAEA, DMAEMA, acrylylcholine (very preferred) and/or methacrylylcholine (preferred), comprising reacting DMEA and/or choline (preferred) and acrylyl-CoA and/or methacrylyl-CoA in the presence of a biocatalyst with choline acetyltransferase activity which is taking place in vitro.

Alternatively, the corresponding process or method taking place in vivo is preferred. Also, the corresponding process or method partially taking place in vitro, partially taking place in vivo is preferred (e.g. where first (meth)acrylyl CoA is formed in vivo, then (e.g. after cell disruption) the (meth) acrylyl CoA is used for the synthesis of DMEA(M)A and/or (meth)acrylylcholine in vitro in the presence of choline acetyltransferase activity, forms a preferred embodiment of the invention.

Another preferred embodiment of the invention relates to said process or method where the biocatalyst with choline acetyltransferase activity is within an organism, especially a (more preferably at least during part of its life cycle unicellular) microorganism, preferably a GMO as defined above. In still one further embodiment, said organism is intact (especially at least viable as defined above), in another embodiment the organism is disrupted or permeabilized.

Yet another preferred embodiment relates to any of the processes or methods described above where the biocatalyst with choline acetyl transferase activity is present in at least partially purified form.

In yet another preferred embodiment of the invention, a process or method as described above wherein the acrylyl CoA and/or methacrylyl CoA is obtained by reacting coenzyme A with acrylate and/or methacrylate in the presence of an energy providing substance, especially ATP, and a biocatalyst with S-acetyl CoA synthetase activity. Preferably, both reactions take place in one pot, preferably during an at least partially overlapping time period, most preferably at the same time. Alternatively, the one pot reaction takes place preferably such that the reaction catalysed by the biocatalyst with S-acetyl CoA synthetase activity takes place first and the products obtainable ((meth)acrylyl CoA) are converted subsequently into DMAEA, DMAEMA, acrylylcholine (very preferred) and/or methacrylylcholine (preferred) using the biocatalyst with choline acetyltransferase activity by reaction with DMAE in free and/or salt form and/or (preferably) a choline salt.

More preferred are all processes and methods mentioned above and below where the biocatalysts are enzymes, especially polypeptides, having the respective activity.

Still more preferred is any process or method described above and below wherein the (meth)acrylyl CoA is produced metabolically, especially from one or more starting materials derived from biomass (especially as described above).

Very preferred is any process or method described above or below where the production of methacrylyl CoA and/or (preferably) acrylyl CoA takes place metabolically (e.g. from free methacrylate and/or acrylate or via other metabolic precursors, such as lactyl CoA) and the conversion with a biocatalyst with choline acetyl transferase activity in the presence of choline and/or DMAE and/or DMAE in salt form, or in each case starting materials for the biosynthesis thereof derived from biomass, to the products are conducted by means of, preferably in, a genetically modified organism (GMO) that is, as far as necessary or desired, modified to comprise the required biocatalytic activities, especially choline acetyltransferase activity and, where required, transporters. Preferably, this process takes place in vivo.

Regarding the GMO transformed with one or more nucleic acids comprising one or more sections coding for and allowing the expression of a biocatalyst with choline acetyltransferase activity, the invention preferably relates to such a GMO which is an insect, an insect tissue or preferably an insect tissue; a plant or a plant tissue; or preferably a (at least during parts of its life cycle unicellular) microorganism, especially a prokaryotic or a fungal microorganism, most preferably a bacterium or a yeast, wherein the nucleic acid comprising one of more sections coding for a biocatalyst with choline acetyltransferase activity is a recombinant nucleic acid.

More preferred is a GMO further comprising a (preferably recombinant) nucleic acid comprising one or more sections coding for one or more transporters appropriate for the transport of one or more starting materials for biocatalytic DMAE (M)A (including the free form and/or salts thereof) and/or preferably (meth)acrylylcholine synthesis into and/or DMAE (M)A and/or preferably (meth)acycrylylcholine out of said microorganism, especially a DMAE and/or especially a choline transporter, more especially one as defined above in more detail.

Still more preferred is a GMO as described in any one of the paragraphs above wherein further to one or more nucleic acids comprising one or more sections coding for a biocatalyst with choline acetyltransferase activity one or more (in one preferred embodiment also recombinant, in another endogenous) nucleic acids comprising one or more sections coding for and allowing for the expression of S-acetyl CoA synthetase are present.

The invention relates especially to the use of the enzymes mentioned in the Examples and/or the processes and reaction conditions described there for the purposes of acrylyl- or methacrylyl CoA and DMAEA, DMAEMA, acrylyl- or methacrylylcholine synthesis.

EXAMPLES

The following Examples serve to illustrate the invention without limiting the scope thereof. H-CoA means the free form of coenzyme A (with the SH group), CoA the corresponding radical bound via —S— without the hydrogen.

Example 1

In Vitro Synthesis of Acrylylcholine in the Presence of Choline Acetyl Transferase and S-Acetyl-CoA Synthetase a) Fed-Batch Acrylyl-CoA Preparation:

Initial Reaction Mixture for Acrylyl-CoA preparation from acrylate and H-CoA in 3.5 ml volume: The reaction is conducted in 3.3 g/100 ml TRIZMA hydrochloride (tris(hydroxymethyl)aminomethane hydrochloride, Sigma) and 0.49 g/100 ml TRIZMA base (pH 7.12 at 37° C.). The other components of the reaction mixture are as follows:

| Component | Concentration (mM) |
| --- | --- |
| $MgCl_2 \cdot 6H_2O$ | 10 |
| Sodium acrylate | 150 |
| ATP | 5 |
| H-CoA | 1 |

S-acetyl CoA synthetase (acetate thiokinase from bakers yeast, Sigma, Saint Louis, Mo., USA; catalogue No. 1765) (1.9 mg/ml) is added. Using the fed-batch approach meaning step-wise addition (feeding) of H-CoA, 15 µl aliquots of H-CoA are added after 5, 10, 15 and 20 minutes, raising the H-CoA concentration by 1 mM each time, and a further 5 mM ATP is added after 25 minutes. Samples are analysed for H-CoA by HPLC (Instrumentation: Agilent Technologies HP1090L with HP1100 Variable Wavelength UV Detector and Chemstation (rev. A.06.01) Data System; column: Luna C18 from Phenomenex, 25 cm×4.6 mm inner diameter, bead diameter 5 μm (No. 92); mobile phase: A: 25 mM ammonium formate (pH 7.0), B: methanol; gradient 5% B for 0 min, then to 30% B in 20 min; flow 1 ml/min (approximately 130 bar), oven temperature 40° C., Detector: UV at 210 nm; injection volume 5 μl, Run time 28 min; peaks are found at the following retention times: ATP approximately 3.710 min, Coenzyme A at approximately 10.554 min, acetyl CoA at approximately 14.457 min, acrylyl CoA at approximately 17.500 min, bisadduct at approximately 15.993 min). When no H-CoA is detected, further 15 μl aliquots of H-CoA are added after 80, 95, 110 and 120 minutes, again raising the H-CoA concentration by 1 mM each time. Further 15 μl aliquots of H-CoA are added after 145 and 155 minutes and sufficient ATP to raise the concentration by 5 mM is added after 150 minutes.

After 150 minutes sufficient H-CoA has been added that, in the absence of a reaction taking place, would have allowed the concentration in the reaction mixture to be raised to 10 mM. A concentration of 1.52 mM acrylyl CoA and 0.47 mM bis-adduct has accumulated in the reaction mixture by this time and no CoA is detected with the HPLC method described above. The relative amount of acrylyl CoA in the combined acrylyl CoA and bis-adduct mixture is 76.5%. The presence of acrylyl CoA and the bisadduct is verified with LC/MS using a column with i.d. 2.0 mm, flow at 0.2 ml/min, using a Finnigan LCQ mass spectrometer in the electrospray ionisation mode.

b) Fed-Batch Preparation of Acrylylcholine:

1.6 ml sample of the above reaction mixture is added to 22.4 mg choline chloride (100 mM). The reaction mixture is briefly incubated at 37° C. and the pH of the reaction mixture is adjusted from pH 6.44 to pH 7.25 by the addition of 4 μl of 2M NaOH. A 0.3 ml sample of the reaction mixture is removed and 40 μl of choline acetyltransferase (recombinant rat choline acetyl transferase AG220 lot 2103 1042, Chemicon International Inc., Temecula, Calif.) is added. Samples (0.5 ml) are taken after 1.75 and 3 hours. Samples are analysed immediately by Ion Chromatography on a Dionex DX-300 Ion Chromatograph with data system software AI-450 v3.3, using a Dionex IonPac CS12A cation-exchange column (4×250 mm) with IonPac CG12A Guard column (4×50 mm), mobile phase: (v/v) 90% 20 mM methanesulphonic acid in water/10% of a 90% (v/v) solution of acetonitrile in water, detection system (Suppressed Conductivity Detection, Cation Self Regenerating Suppressor (CSRS-Ultra) in the autosuppression external water mode, Dionex Corporation, Sunnyvale, Calif. USA).

When the reaction mixture is incubated with choline acetyltransferase for 1.75 hours a peak appears (retention time approximately 11 to 11.5 min) that is identified as acrylylcholine by Ion Chromatography as described. The estimated acrylylcholine concentration from this peak is 0.14 mM. The estimated molar yield (based on starting acrylyl CoA) is therefore 35%.

The invention claimed is:

1. A process for the production of acrylylcholine, methacrylylcholine, 2-(N,N-dimethylamino)ethyl acrylate or 2-(N,N-dimethylamino)ethyl methacrylate comprising
    a) reacting choline with acrylyl-CoA or methyacrylyl-CoA and choline acetyltransferase to produce acrylylcholine or methylacrylylcholine, respectively; or
    b) reacting acrylyl-CoA or methyacrylyl-CoA with 2-(N,N-dimethylamino) ethanol and choline acetyltransferase to produce 2-(N,N-dimethylamino)ethyl acrylate or 2-(N,N-dimethylamino)ethyl methacrylate, respectively.

2. The process according to claim 1 wherein the source of the choline acetyltransferase is an organism that is disrupted with a surfactant.

3. The process according to claim 1 wherein the choline acetyl transferase is at least partially purified.

4. The process according to claim 1 wherein the acrylyl CoA or methacrylyl CoA is obtained by reacting coenzyme A with acrylate or methacrylate, respectively, ATP and S-acetyl CoA synthetase.

5. The process according to claim 4, wherein the reaction catalyzed by choline acetyltransferase and the reaction catalyzed by S-acetyl CoA synthetase takes place in one pot.

6. The process according to claim 5 wherein the reaction catalyzed by S-acetyl CoA synthetase takes place first and the products obtained thereby are converted into acrylylcholine or methacrylylcholine, respectively, by choline acetyltransferase.

* * * * *